United States Patent [19]

Brannigan et al.

[11] 4,243,406

[45] Jan. 6, 1981

[54] 5-ARYL-4-ISOXAZOLECARBOXYLATE-SAFENING AGENTS

[75] Inventors: Lawrence H. Brannigan, Olivette; John E. Franz, Crestwood; David E. Schafer, Creve Coeur, all of Mo.

[73] Assignee: Monsanto Company, St. Louis, Mo.

[21] Appl. No.: 973,413

[22] Filed: Dec. 26, 1978

[51] Int. Cl.$^3$ .................... A01N 43/26; A01N 37/22; A01N 37/24
[52] U.S. Cl. .......................................... 71/88; 71/118
[58] Field of Search ...................... 71/88, 118

[56] References Cited

U.S. PATENT DOCUMENTS

| 3,442,945 | 5/1969 | Olin | 71/118 |
| 3,547,620 | 12/1970 | Olin | 71/118 |
| 3,884,671 | 5/1975 | Albright et al. | 71/88 |
| 3,937,730 | 2/1976 | Vogel et al. | 71/118 |
| 3,989,503 | 11/1976 | Pallos et al. | 71/88 |
| 4,003,735 | 1/1977 | Czajkowski et al. | 71/88 |
| 4,033,756 | 7/1977 | Hoffmann | 71/88 |
| 4,144,047 | 3/1979 | Franz et al. | 71/88 |

*Primary Examiner*—Glennon H. Hollrah
*Attorney, Agent, or Firm*—William T. Black; Donald W. Peterson

[57] ABSTRACT

The invention relates to the safening of crop plants to the use of herbicides using a 5-aryl-4-isoxazolecarboxylate or composition containing such compounds to reduce the herbicidal injury to treated crop plants. The invention is also concerned with novel compositions which comprise an acetanilide herbicide and a 5-aryl-4-isoxazolecarboxylate.

43 Claims, No Drawings

5-ARYL-4-ISOXAZOLECARBOXYLATE-SAFENING AGENTS

This invention relates to the safening of crop plants to the use of herbicides using a safening agent or composition containing a safening agent to reduce the herbicidal injury to treated crop plants. More specifically, the invention is concerned with the methods of treating the plant crop locus with a 5-aryl-4-isoxazolecarboxylate derivative or composition thereof in order to prevent or reduce the injury to the crop plant which would otherwise occur due to the use of an acetanilide herbicide alone. This invention is also concerned with novel compositions which comprise an acetanilide herbicide and a 5-aryl-4-isoxazolecarboxylate derivative.

In practice it has been found that acetanilide herbicides are effective in controlling certain weeds in the presence of growing crops. However, when applied at rates necessary to stunt or kill the weeds, many of the acetanilide herbicides injure certain crop plants thus slowing proper growth and development. This results in decreased crop yields, thereby reducing the effectiveness of certain herbicides in controlling weeds in the presence of crops. Obviously, a safening agent or composition thereof, that could be used to treat the crop plant locus, resulting in a reduction of injury due to application of the herbicide without a corresponding reduction of herbicidal action on the weed, would be quite beneficial.

In accordance with the novel aspects of the present invention, crop plants can be protected or the tolerance of said crop plants can be increased to minimize injury due to the application thereto of an acetanilide herbicide, without a corresponding reduction in injury to the weeds by treating the crop plant locus with an effective amount of a safening agent comprising a 5-aryl-4-isoxazolecarboxylate or derivative thereof, having the formula

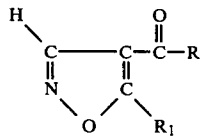

wherein R is selected from the group consisting of hydroxyl, lower alkoxy, lower alkoxyalkoxy, lower alkoxyalkoxyalkoxy, lower haloalkoxy, amino and halogen and $R_1$ is selected from the group consisting of phenyl and phenyl substituted with up to three groups individually selected from the class consisting of lower alkyl, lower alkoxy, lower haloalkyl, nitro and halogen.

The class of acetanilide herbicides employed in the compositions and methods of this invention include 2-chloro-2′,6′-diethyl-N-(methoxymethyl)acetanilide, 2-chloro-2′,6′-diethyl-N-(butoxymethyl)acetanilide, 2-chloro-N-(2-methoxy-1-methylethyl)-6′-ethyl-o-acetotoluidide and the like. The preparation and use of 2-chloro-2′,6′-diethyl-N-(methoxymethyl)acetanilide and 2-chloro-2′,6′-diethyl-N-(butoxymethyl)acetanilide to control the growth of undesired plants is described in U.S. Pat. No. 3,442,945. Herbicidal compositions containing these compounds are disclosed in U.S. Pat. No. 3,547,620. U.S. Pat. No. 3,937,730 discloses 2-chloro-N-(2-methoxy-1-methylethyl)-6′-ethyl-o-acetotoluidide.

Treatment of the crop plant locus refers to the application of the herbicide and safening agent, in admixture or in sequence, to the plant growth medium as well as directly to the plants or to parts thereof such as roots, stems, leaves, flowers, fruits or other plant parts. Also included in the term is treatment of plant seeds prior to planting with a safening agent.

As employed herein, the term "lower" designates those aliphatic hydrocarbon radicals which have up to four carbon atoms in a straight or branched chain. Groups representative of these radicals include for example, methyl, ethyl, propyl, isopropyl, butyl, isobutyl, t-butyl and the like.

The term "halogen" as used herein includes chloro, bromo, fluoro and iodo.

Illustrative of the substituted phenyl groups which $R_1$ represents are monosubstituted phenyl wherein the substituent is in the ortho, meta or para position, for example, methylphenyl, butylphenyl, methoxyphenyl, butoxyphenyl, fluorophenyl, chlorophenyl, bromophenyl, iodophenyl, trifluoromethylphenyl, nitrophenyl and the like and the di- and tri-substituted phenyl groups wherein the substituents are the same or different and are located in the 2,3,4,5 or 6 positions of the phenyl ring, for example, dichlorophenyl, difluorophenyl, methylchlorophenyl, butoxy fluorophenyl, (methyl) (butyl)phenyl, (methoxy) (butoxy)phenyl, dimethoxyphenyl, methyl nitrophenyl, trichlorophenyl, trimethylphenyl, tributoxyphenyl and the like.

Representative of the haloalkoxy groups represented by R are fluoromethoxy, chloroethoxy, fluoroethoxy, fluoropropoxy, chlorobutoxy and the like.

The term "haloalkyl" is understood to mean those alkyl moieties having up to four carbon atoms wherein at least one hydrogen atom has been replaced by a halogen atom. Specifically included are those alkyl moieties in which all of the hydrogen atoms have been replaced by halogen atoms, such as trifluoromethyl.

The safening agents of this invention may be applied in a mixture with the above-named herbicides, or the components of the mixture can be used sequentially. In the case of a sequential treatment, the safening agent may be applied either before or after application of the herbicide. Effective herbicidal amounts of the active ingredients are well understood by those skilled in the art, and such amounts are used together with an effective safening amount of a 5-aryl-4-isoxazolecarboxylate or derivative thereof. The term effective safening amount refers to the amount of safening agent required to effectively reduce the crop injury caused by application of a herbicide at a given rate. The amount of safening agent employed in the method and compositions of this invention will vary depending upon the particular herbicide with which the safening agent is employed, the rate of application of the herbicide, the crop to be protected as well as the manner of application of the safening agent. The ratio of herbicide to safening agent may vary depending upon the age of the plants at time of treatment, climatic conditions, soil, etc. It is generally preferred, however, to employ a weight ratio of herbicide to safening agent ranging from about 1:8 to 8:1, although ratios of from 1:32 to 32:1 are shown to be effective in the tests below.

In each test a crop plant, with or without weeds, is grown in a container, and there is an application of the herbicide and a safening agent. In each test there is also a container which receives no application at all, a container to which only the herbicide is applied, and a container to which only the safening agent is applied.

The untreated container shows normal plant growth as standard, and it also serves as an indicator of extraneous conditions which may affect the plants. The other containers show the effect of the herbicide alone, the effect of the safening agent alone, and the effect of the application of both. These effects are in terms of percent inhibition of plant growth relative to the plants in the untreated container.

The "safening effect" is determined by adding the percent inhibition obtained when the herbicide is applied alone to the percent inhibition obtained when the safening agent is applied alone (in no instance, however, will this sum be taken as greater than 100), then substracting from that sum the percent inhibition obtained when the herbicide and safening agent are both applied. The percent inhibition as used hereinafter refers to the percent of weeds or crop plants which are injured or killed.

The effectiveness of the 5-aryl-4-isoxazolecarboxylates for the purposes of this invention is demonstrated by the results obtained using the various test procedures hereinafter described. Specific individual compounds employed in these procedures are identified by the example number in which their preparation is described. The herbicide as used in the test procedures was in the form of a formulation comprising the named active ingredient, a solvent and an emulsifier. All rates of application of the herbicide and safening agent in the following examples are shown in kilograms per hectare unless otherwise noted. An asterisk indicates a safening effect of 0 to 19%. In those tests where the procedures are replicated, the results represent an average of all replicates. The compounds as employed in the following examples serve only to illustrate the novel aspects of the invention and should not be construed as a limitation on its scope.

EXAMPLE 1

A good grade of top soil was placed in a container and compacted to a depth of approximately 1.27 cm. from the top of said container. A predetermined number of seeds of each of the crop species to be tested were placed on top of the soil. A quantity of soil sufficient to substantially fill the container was measured and placed in a second container. A measured quantity of the safening agent dispersed or dissolved in a suitable carrier was applied to the soil in the second container. A measured quantity of formulated 2-chloro-2',6'-diethyl-N-(butoxymethyl)acetanilide dispersed or dissolved in a suitable carrier was then sprayed on the soil previously treated with the safening agent. The soil containing the safening agent and herbicide was thoroughly mixed. This mixing is sometimes referred to as incorporation of the herbicide and safening agent into the soil. The mixing or incorporation provides a substantially uniform distribution of the safening agent and herbicide throughout the soil. The seeds were covered with the soil containing the safening agent and herbicide and the pots were leveled. The pots were then placed on a sand bench in the greenhouse and watered from below as needed. The plants were observed at the end of approximately 21 days and the results in terms percent inhibition of each seed lot were recorded.

The test results in Table I illustrate the reduction in the inhibition of crop plants which was achieved when 2-chloro-2',6'-diethyl-N-(butoxymethyl) acetanilide was used in conjunction with a safening agent of this invention.

TABLE I

| SAFENING AGENT | SAFENING AGENT RATE | HERBICIDE RATE | SAFENING EFFECT | | |
|---|---|---|---|---|---|
| | | | RICE | SORGHUM | WHEAT |
| 12 | 8.96 | 4.48 | 83 | 68 | 43 |
| 13 | 8.96 | 4.48 | 48 | * | 28 |
| 14 | 8.96 | 4.48 | 70 | 63 | 33 |
| 15 | 8.96 | 4.48 | 43 | 58 | 23 |
| 16 | 4.48 | 4.48 | 40 | 49 | 35 |
| | 8.96 | 4.48 | 38 | 77 | 30 |
| | 8.96 | 4.48 | 73 | 63 | 43 |
| | 8.96 | 4.48 | 94 | 52 | 58 |
| 17 | 8.96 | 4.48 | 43 | 28 | 23 |
| 18 | 4.48 | 4.48 | 50 | 44 | * |
| 19 | 8.96 | 4.48 | * | 38 | * |
| | 8.96 | 6.72 | * | * | 20 |
| 20 | 8.96 | 4.48 | 20 | * | * |
| 21 | 8.96 | 4.48 | 50 | 32 | 20 |
| 22 | 8.96 | 6.72 | 35 | * | 45 |
| 23 | 8.96 | 6.72 | * | 25 | 35 |
| 24 | 8.96 | 4.48 | 65 | 25 | * |
| 25 | 8.96 | 4.48 | 50 | * | * |
| 26 | 8.96 | 4.48 | 38 | 65 | * |
| 27 | 8.96 | 6.72 | 67 | * | 55 |
| 28 | 8.96 | 6.72 | * | * | 20 |
| 29 | 8.96 | 6.72 | 45 | 40 | 50 |
| 30 | 8.96 | 6.72 | 33 | * | 20 |
| 31 | 8.96 | 6.72 | * | 25 | 30 |
| 32 | 8.96 | 6.72 | 40 | * | * |
| 33 | 8.96 | 6.72 | 38 | * | * |
| 34 | 8.96 | 6.72 | 65 | * | 45 |
| 35 | 8.96 | 6.72 | 63 | 45 | 25 |
| 36 | 8.96 | 6.72 | 38 | 20 | 40 |
| 37 | 8.96 | 6.72 | 45 | 20 | * |
| 38 | 8.96 | 6.72 | 48 | * | 30 |

EXAMPLE 2

A good grade of top soil was placed in a plastic pot. A measured quantity of the safening agent dispersed or dissolved in a suitable carrier was sprayed on the soil surface. A measured quantity of formulated 2-chloro-2',6'-diethyl-N-(butoxymethyl)acetanilide dispersed or dissolved in a suitable carrier was sprayed on the soil surface. Presoaked rice was seeded into the pots that were previously flooded with water. The water level was lowered to the soil surface after 24 hours and maintained at this level for 5 days after which the pots were reflooded for the duration of the test. The plants were observed at the end of approximately 21 days and the results in terms of the percent inhibition of rice are recorded.

The test results in Table II further illustrate the reduction in the inhibition of rice plants which was achieved when 2-chloro-2',6'-diethyl-N-(butoxymethyl)acetanilide was used in conjunction with a safening agent of this invention. Individual data was not included at application rates at which the herbicide did not produce any crop injury.

TABLE II

| SAFENING AGENT | SAFENING AGENT RATE | HERBICIDE RATE | SAFENING EFFECT |
|---|---|---|---|
| 12 | 0.56 | 0.07 | 45 |
| | 0.56 | 0.28 | 71 |
| | 0.56 | 1.12 | 20 |
| | 0.56 | 0.07 | 34 |
| | 0.56 | 0.28 | 85 |
| | 0.56 | 1.12 | 32 |
| | 0.56 | 0.07 | 35 |
| | 0.56 | 0.28 | 72 |
| | 0.56 | 1.12 | 57 |
| | 0.56 | 0.07 | 26 |

TABLE II-continued

| SAFENING AGENT | SAFENING AGENT RATE | HERBICIDE RATE | SAFENING EFFECT |
|---|---|---|---|
| | 0.56 | 0.28 | 50 |
| | 0.56 | 1.12 | 45 |
| | 0.56 | 0.07 | 74 |
| | 0.56 | 0.28 | 92 |
| | 0.56 | 1.12 | 35 |
| | 0.56 | 0.07 | 85 |
| | 0.56 | 0.28 | 85 |
| | 0.56 | 1.12 | 52 |
| | 1.12 | 0.14 | 44 |
| | 1.12 | 0.56 | 84 |
| 13 | 1.12 | 0.14 | 44 |
| | 1.12 | 0.56 | 79 |
| 14 | 1.12 | 0.14 | 44 |
| | 1.12 | 0.56 | 24 |
| 15 | 1.12 | 0.14 | 44 |
| | 1.12 | 0.56 | 66 |
| 16 | 0.56 | 0.07 | 49 |
| | 0.56 | 0.28 | 85 |
| | 0.56 | 1.12 | * |
| | 0.56 | 0.07 | 63 |
| | 0.56 | 0.28 | 61 |
| | 0.56 | 1.12 | * |
| | 1.12 | 0.14 | 78 |
| | 1.12 | 0.56 | 84 |
| | 1.12 | 0.035 | 81 |
| 16 | 1.12 | 0.14 | 99 |
| | 1.12 | 0.56 | 90 |
| 17 | 1.12 | 0.14 | 44 |
| | 1.12 | 0.56 | 29 |
| 18 | 1.12 | 0.035 | 61 |
| | 1.12 | 0.14 | 30 |
| | 1.12 | 0.56 | * |
| 20 | 0.56 | 0.07 | * |
| | 0.56 | 0.28 | * |
| | 0.56 | 1.12 | * |
| 21 | 0.56 | 0.07 | 28 |
| | 0.56 | 0.28 | 55 |
| | 0.56 | 1.12 | 25 |
| 25 | 0.56 | 0.07 | * |
| | 0.56 | 0.28 | * |
| | 0.56 | 1.12 | * |
| 26 | 1.12 | 0.14 | * |
| | 1.12 | 0.56 | * |
| 27 | 0.56 | 0.07 | 30 |
| | 0.56 | 0.28 | 67 |
| | 0.56 | 1.12 | * |
| 29 | 0.56 | 0.07 | * |
| | 0.56 | 0.28 | * |
| | 0.56 | 1.12 | * |

EXAMPLE 3

The procedure of Example 1 was employed utilizing 2-chloro-2',6'-diethyl-N-(methoxymethyl)acetanilide in lieu of 2-chloro-2',6'-diethyl-N-(butoxymethyl) acetanilide as the herbicide.

The test results in Table III illustrate the reduction in the inhibition of crop plants which was achieved when 2-chloro-2',6'-diethyl-N-(methoxymethyl) acetanilide was used in conjunction with a safening agent of this invention.

TABLE III

| SAFENING AGENT | SAFENING AGENT RATE | HERBICIDE RATE | SAFENING EFFECT RICE | SORGHUM | WHEAT |
|---|---|---|---|---|---|
| 12 | 8.96 | 4.48 | 55 | 64 | 58 |
| 13 | 8.96 | 4.48 | * | * | * |
| 14 | 8.96 | 4.48 | * | 59 | 73 |
| 15 | 8.96 | 4.48 | * | 24 | 38 |
| 16 | 4.48 | 2.24 | 30 | 65 | 30 |
| | 8.96 | 4.48 | 85 | 69 | 43 |
| | 8.96 | 4.48 | 35 | 39 | 78 |

TABLE III-continued

| SAFENING AGENT | SAFENING AGENT RATE | HERBICIDE RATE | SAFENING EFFECT RICE | SORGHUM | WHEAT |
|---|---|---|---|---|---|
| | 8.96 | 4.48 | * | 64 | 45 |
| 17 | 8.96 | 4.48 | * | * | * |
| 18 | 4.48 | 2.24 | * | 55 | * |
| 19 | 8.96 | 4.48 | * | * | * |
| | 8.96 | 2.24 | * | * | * |
| 20 | 8.96 | 2.24 | * | * | * |
| 21 | 8.96 | 2.24 | 72 | * | 40 |
| 22 | 8.96 | 2.24 | 44 | 35 | 30 |
| 23 | 8.96 | 2.24 | 79 | 35 | 20 |
| 24 | 8.96 | 2.24 | 88 | 30 | * |
| 25 | 8.96 | 2.24 | * | * | * |
| 26 | 8.96 | 4.48 | * | 24 | 23 |
| 27 | 8.96 | 4.48 | * | * | 38 |
| 28 | 8.96 | 2.24 | * | * | * |
| 29 | 8.96 | 4.48 | * | * | * |
| 30 | 8.96 | 2.24 | * | 25 | * |
| 31 | 8.96 | 2.24 | * | 30 | 20 |
| 32 | 8.96 | 2.24 | * | * | 35 |
| 33 | 8.96 | 2.24 | 65 | 25 | * |
| 34 | 8.96 | 2.24 | 45 | 28 | * |
| 35 | 8.96 | 2.24 | 78 | 60 | * |
| 36 | 8.96 | 2.24 | 20 | 40 | 45 |
| 37 | 8.96 | 2.24 | 20 | 30 | * |
| 38 | 8.96 | 2.24 | 40 | * | * |

EXAMPLE 4

The procedure of Example 1 was employed utilizing 2-chloro-2',6'-diethyl-N-(methoxymethyl)acetanilide in lieu of 2-chloro-2',6'-diethyl-N-(butoxymethyl) acetanilide as the herbicide.

The test results in Table IV illustrate the reduction in the inhibition of crop plants which was achieved when 2-chloro-2',6'-diethyl-N-(methoxymethyl) acetanilide at various application rates was used in conjunction with a safening agent of this invention. Individual data was not included at application rates at which the herbicide did not produce any crop injury.

TABLE IV

| SAFENING AGENT | SAFENING AGENT RATE | HERBICIDE RATE | SAFENING EFFECT RICE | SORGHUM | WHEAT |
|---|---|---|---|---|---|
| 12 | 8.96 | 0.56 | 65 | 89 | 20 |
| | 8.96 | 1.12 | 75 | 84 | 40 |
| | 8.96 | 2.24 | 30 | 65 | 38 |
| | 8.96 | 4.48 | 59 | 60 | 55 |
| 14 | 8.96 | 0.56 | 65 | 90 | 20 |
| | 8.96 | 1.12 | 65 | 85 | 40 |
| | 8.96 | 2.24 | 55 | 80 | 53 |
| | 8.96 | 4.48 | 30 | 50 | 60 |
| 16 | 4.48 | 1.12 | | 40 | |
| | 4.48 | 2.24 | | 38 | |
| | 4.48 | 4.48 | 33 | 68 | |
| 18 | 4.48 | 1.12 | | 25 | |
| | 4.48 | 2.24 | | * | |
| | 4.48 | 4.48 | 28 | 23 | |
| 21 | 8.96 | 0.56 | 88 | 30 | * |
| | 8.96 | 1.12 | 80 | 45 | * |
| | 8.96 | 2.24 | 68 | 30 | * |
| | 8.96 | 4.48 | 58 | 40 | * |
| 22 | 8.96 | 0.56 | 20 | 25 | 20 |
| | 8.96 | 1.12 | 50 | 70 | 40 |
| | 8.96 | 2.24 | 55 | 75 | 50 |
| | 8.96 | 4.48 | 55 | 65 | 40 |
| 23 | 8.96 | 0.56 | 20 | 35 | 20 |
| | 8.96 | 1.12 | 25 | 70 | 30 |
| | 8.96 | 2.24 | 55 | 55 | 20 |
| | 8.96 | 4.48 | 70 | 40 | 40 |
| 27 | 8.96 | 0.56 | * | 65 | 70 |
| | 8.96 | 1.12 | 30 | 69 | 30 |

TABLE IV-continued

| SAFENING AGENT | SAFENING AGENT RATE | HERBICIDE RATE | SAFENING EFFECT | | |
|---|---|---|---|---|---|
| | | | RICE | SORGHUM | WHEAT |
| | 8.96 | 2.24 | * | 59 | 39 |
| | 8.96 | 4.48 | * | * | * |
| 34 | 8.96 | 0.56 | 30 | 40 | * |
| | 8.96 | 1.12 | 35 | 60 | * |
| | 8.96 | 2.24 | 65 | 35 | 25 |
| | 8.96 | 4.48 | 20 | * | * |

EXAMPLE 5

A good grade of soil was placed in a container and compacted to a depth of approximately 1.27 cm. from the top of said container. A predetermined number of sugar beet, rice, wheat, sorghum, soybeans, corn and cotton seeds were applied to the soil surface. The seeds were then covered with a top soil that had been previously treated by applying a formulated acetanilide herbicide then a safening agent to the soil and incorporating the herbicide and safening agent therein. The herbicide and safener were applied in amounts sufficient to give the indicated application rates. The plants were observed at the end of approximately 21 days and the results recorded.

The test results in Table V illustrate the reduction in the inhibition of crop plants which was achieved when an acetanilide herbicide was used in conjunction with a safening agent of this invention. Individual data was not included at application rates at which herbicide did not produce any crop injury.

TABLE V

| HERBICIDE | HERBICIDE RATE | SAFENING AGENT | SAFENING AGENT RATE | SAFENING EFFECT | | | | | | |
|---|---|---|---|---|---|---|---|---|---|---|
| | | | | Sugar Beets | Rice | Wheat | Sorghum | Soybeans | Corn | Cotton |
| 2-Chloro-2'-6'-diethyl-N-(methoxymethyl)acetanilide | 0.56 | 16 | 8.96 | * | 93 | 85 | 50 | * | * | |
| | 4.48 | | 8.96 | * | 20 | 30 | 21 | * | * | 22 |
| 2-Chloro-2'-6'-diethyl-N-(butoxymethyl)acetanilide | 1.12 | 16 | 8.96 | * | 20 | 43 | 25 | * | * | * |
| | 8.96 | | 8.96 | * | 80 | 68 | 57 | * | * | * |
| 2-Chloro-N-(2-methoxy-1-methylethyl)-6'-ethyl-o-acetotoluidide | 0.56 | 16 | 8.96 | * | 48 | 43 | 35 | | | |
| | 4.48 | | 8.96 | * | 25 | 50 | * | * | 33 | * |

As noted previously, the 5-aryl-4-isoxazolecarboxylates may be used to protect crops from the herbicidal injury without a corresponding diminution in the high level of weed control demonstrated by the herbicides. Examples 6-9 are illustrative of such activity.

EXAMPLE 6

5.08 cm. of a good grade of top soil was placed in a 7.62 cm. deep plastic pot. A predetermined number of barnyardgrass seeds were applied to the soil surface. A measured quantity of the safening agent dispersed or dissolved in a suitable carrier was sprayed on the soil surface. A measured quantity of formulated 2-chloro-2',6'-diethyl-N-(butoxymethyl) acetanilide dissolved in a solvent was sprayed on the soil surface. Pre-soaked rice was seeded into the pots that were previously flooded with water. The water level was lowered to the soil surface after 24 hours and maintained at this level for 7 days after which the pots were reflooded for the duration of the test. The plants were observed approximately 21 days after treatment.

Tables VI and VII summarize the results of two separate tests conducted in accordance with this procedure.

TABLE VI

| SAFENING AGENT | SAFENING AGENT RATE | HERBICIDE RATE | PERCENT INHIBITION | |
|---|---|---|---|---|
| | | | RICE | BARNYARDGRASS |
| — | — | 0.07 | 65 | 95 |
| — | — | 0.28 | 93 | 100 |
| — | — | 1.12 | 100 | 100 |
| 12 | 0.56 | — | 0 | 0 |
| | 0.56 | 0.07 | 0 | 90 |
| | 0.56 | 0.28 | 35 | 100 |
| | 0.56 | 1.12 | 75 | 100 |
| 32 | 0.56 | — | 0 | 0 |
| | 0.56 | 0.07 | 83 | 100 |
| | 0.56 | 0.28 | 95 | 100 |
| | 0.56 | 1.12 | 100 | 100 |
| 34 | 0.56 | — | 0 | 0 |
| | 0.56 | 0.07 | 63 | 98 |
| | 0.56 | 0.28 | 88 | 100 |
| | 0.56 | 1.12 | 100 | 100 |

TABLE VII

| SAFENING AGENT | SAFENING AGENT RATE | HERBICIDE RATE | PERCENT INHIBITION | |
|---|---|---|---|---|
| | | | RICE | BARNYARD GRASS |
| — | — | 0.07 | 31 | 99 |
| — | — | 0.28 | 74 | 100 |
| — | — | 1.12 | 98 | 100 |
| 12 | 0.07 | — | 0 | 0 |
| | 0.07 | 0.07 | 0 | 99 |
| | 0.07 | 0.28 | 38 | 99 |

TABLE VII-continued

| SAFENING AGENT | SAFENING AGENT RATE | HERBICIDE RATE | PERCENT INHIBITION RICE | BARNYARD GRASS |
|---|---|---|---|---|
|  | 0.07 | 1.12 | 93 | 100 |
| 12 | 0.28 | — | 0 | 0 |
|  | 0.28 | 0.07 | 0 | 90 |
|  | 0.28 | 0.28 | 10 | 100 |
|  | 0.28 | 1.12 | 70 | 100 |
| 12 | 1.12 | — | 0 | 0 |
|  | 1.12 | 0.07 | 0 | 90 |
|  | 1.12 | 0.28 | 0 | 100 |
|  | 1.12 | 1.12 | 38 | 100 |

EXAMPLE 7

A good grade of top soil was placed in a plastic pot and compacted to a depth of approximately 1.27 cm. from the top of said pot. A predetermined number of rice seeds and barnyardgrass weed seeds were placed on top of the soil. A cover layer, approximately 1.27 cm., was placed on top of said seeds. A measured quantity of the safening agent dispersed or dissolved in a suitable carrier was sprayed on the soil surface. A measured quantity of formulated 2-chloro-2',6'-diethyl-N-(butoxymethyl)acetanilide dispersed on dissolved in a suitable carrier was sprayed on the soil surface. The pots were given overhead water and subirrigated as required for the duration of the test. The plants were observed approximately 21 days after treatment.

The test results in Table VIII further illustrate the reduction in the inhibition of rice plants, and also the continued high level of weed control, which was achieved when 2-chloro-2',6'-diethyl-N-(butoxymethyl)acetanilide was used in conjunction with a safening agent of this invention. This test also included application of the herbicide at rates of 0.035, 0.14 and 0.56 kilograms per hectare, but the individual data was not included here since the herbicide alone caused no inhibition of rice plants at these rates in this test procedure.

TABLE VIII

| SAFENING AGENT | SAFENING AGENT RATE | HERBICIDE RATE | PERCENT INHIBITION RICE | BARNYARDGRASS |
|---|---|---|---|---|
| — | — | 2.24 | 20 | 100 |
| — | — | 4.48 | 78 | 100 |
| — | — | 8.96 | 93 | 100 |
| 16 | 0.14 | — | 0 | 0 |
|  | 0.14 | 2.24 | 50 | 100 |
|  | 0.14 | 4.48 | 68 | 99 |
|  | 0.14 | 8.96 | 90 | 100 |
|  | 1.12 | — | 0 | 0 |
|  | 1.12 | 2.24 | 5 | 100 |
|  | 1.12 | 4.48 | 65 | 100 |
|  | 1.12 | 8.96 | 93 | 100 |
|  | 8.96 | — | 0 | 0 |
|  | 8.96 | 2.24 | 0 | 100 |
|  | 8.96 | 4.48 | 8 | 100 |
|  | 8.96 | 8.96 | 43 | 100 |

EXAMPLE 8

5.08 cm. of a good grade of top soil was placed in a 7.62 cm. deep plastic pot. A predetermined number of barnyardgrass seeds were placed on top of the soil. A cover layer, approximately 1.27 cm., was placed on top of said seeds. The soil was then treated with a mixture of the safening agent and formulated 2-chloro-2',6'-diethyl-N-(butoxymethyl)acetanilide dispersed or dissolved in a suitable solvent. Pre-soaked rice was seeded into pots that had been previously flooded with water. The water level was lowered to the soil surface after 24 hours and maintained at or below this level for 6 days after which the pots were reflooded for the duration of the test. The percent inhibition was observed approximately 21 days after treatment.

Tables IX-XIV summarize the results of seven separate tests conducted in accordance with this procedure.

TABLE IX

| SAFENING AGENT | SAFENING AGENT RATE | HERBICIDE RATE | PERCENT INHIBITION RICE | BARNYARDGRASS |
|---|---|---|---|---|
|  |  | 0.07 | 64 | 100 |
|  |  | 0.28 | 78 | 100 |
|  |  | 1.12 | 100 | 100 |
| 12 | 0.07 | — | 0 | 5 |
|  | 0.07 | 0.07 | 5 | 90 |
|  | 0.07 | 0.28 | 55 | 100 |
|  | 0.07 | 1.12 | 93 | 100 |
|  | 0.28 | — | 0 | 5 |
|  | 0.28 | 0.07 | 0 | 95 |
|  | 0.28 | 0.28 | 40 | 100 |
|  | 0.28 | 1.12 | 65 | 100 |
|  | 1.12 | — | 0 | 0 |
|  | 1.12 | 0.07 | 0 | 98 |
|  | 1.12 | 0.28 | 23 | 99 |
|  | 1.12 | 1.12 | 73 | 100 |

TABLE X

| SAFENING AGENT | SAFENING AGENT RATE | HERBICIDE RATE | PERCENT INHIBITION RICE | BARNYARDGRASS |
|---|---|---|---|---|
| — |  | 0.07 | 56 | 91 |
|  |  | 0.28 | 94 | 99 |
|  |  | 1.12 | 100 | 100 |
| 12 | 0.07 | — | 0 | 0 |
|  | 0.07 | 0.07 | 5 | 88 |
|  | 0.07 | 0.28 | 48 | 99 |
|  | 0.07 | 1.12 | 99 | 100 |
|  | 0.28 | — | 0 | 0 |
|  | 0.28 | 0.07 | 3 | 83 |
|  | 0.28 | 0.28 | 18 | 100 |
|  | 0.28 | 1.12 | 78 | 100 |
|  | 1.12 | — | 0 | 0 |
|  | 1.12 | 0.07 | 0 | 97 |
|  | 1.12 | 0.28 | 0 | 99 |
|  | 1.12 | 1.12 | 33 | 100 |

TABLE XI

| SAFENING AGENT | SAFENING AGENT RATE | HERBICIDE RATE | PERCENT INHIBITION RICE | BARNYARDGRASS |
|---|---|---|---|---|
|  |  | 0.018 | 29 | 91 |
|  |  | 0.07 | 63 | 99 |
|  |  | 0.28 | 92 | 100 |
|  |  | 1.12 | 100 | 100 |
| 12 | 0.07 | — | 0 | 0 |
|  | 0.07 | 0.018 | 0 | 75 |
|  | 0.07 | 0.07 | 15 | 97 |
|  | 0.07 | 0.28 | 60 | 100 |
|  | 0.07 | 1.12 | 96 | 100 |
|  | 0.14 | — | 0 | 0 |
|  | 0.14 | 0.018 | 0 | 85 |
|  | 0.14 | 0.07 | 0 | 99 |
|  | 0.14 | 0.28 | 45 | 100 |
|  | 0.14 | 1.12 | 98 | 100 |
|  | 0.28 | — | 0 | 0 |
|  | 0.28 | 0.018 | 0 | 85 |

TABLE XI-continued

| SAFENING AGENT | SAFENING AGENT RATE | HERBICIDE RATE | PERCENT INHIBITION RICE | PERCENT INHIBITION BARNYARDGRASS |
|---|---|---|---|---|
| | 0.28 | 0.07 | 20 | 95 |
| | 0.28 | 0.28 | 20 | 100 |
| | 0.28 | 1.12 | 85 | 100 |
| | 0.56 | — | 0 | 0 |
| | 0.56 | 0.018 | 0 | 70 |
| | 0.56 | 0.07 | 0 | 94 |
| | 0.56 | 0.28 | 23 | 100 |
| | 0.56 | 1.12 | 35 | 100 |
| | 1.12 | — | 0 | 0 |
| | 1.12 | 0.018 | 0 | 75 |
| | 1.12 | 0.07 | 0 | 83 |
| | 1.12 | 0.28 | 0 | 100 |
| | 1.12 | 1.12 | 33 | 100 |
| 16 | 0.07 | — | 0 | 0 |
| | 0.07 | 0.018 | 5 | 95 |
| | 0.07 | 0.07 | 33 | 98 |
| | 0.07 | 0.28 | 80 | 100 |
| | 0.07 | 1.12 | 100 | 100 |
| | 0.14 | — | 0 | 0 |
| | 0.14 | 0.018 | 0 | 88 |
| | 0.14 | 0.07 | 0 | 97 |
| | 0.14 | 0.28 | 70 | 100 |
| | 0.14 | 1.12 | 99 | 100 |
| | 0.28 | — | 0 | 0 |
| | 0.28 | 0.018 | 0 | 78 |
| | 0.28 | 0.07 | 15 | 97 |
| | 0.28 | 0.28 | 40 | 100 |
| | 0.28 | 1.12 | 88 | 100 |
| | 0.56 | — | 0 | 0 |
| | 0.56 | 0.018 | 0 | 63 |
| | 0.56 | 0.07 | 0 | 94 |
| | 0.56 | 0.28 | 20 | 100 |
| | 0.56 | 1.12 | 53 | 100 |
| | 1.12 | — | 0 | 0 |
| | 1.12 | 0.018 | 0 | 80 |
| | 1.12 | 0.07 | 0 | 96 |
| | 1.12 | 0.28 | 3 | 100 |
| | 1.12 | 1.12 | 58 | 100 |

TABLE XII[1]

| SAFENING AGENT | SAFENING AGENT RATE | HERBICIDE RATE | PERCENT INHIBITION RICE | PERCENT INHIBITION BARNYARDGRASS |
|---|---|---|---|---|
| | | 0.07 | 23 | 98 |
| | | 0.28 | 78 | 100 |
| | | 1.12 | 99 | 100 |
| 12 | 0.07 | — | 0 | 0 |
| | 0.07 | 0.07 | 8 | 100 |
| | 0.07 | 0.28 | 40 | 100 |
| | 0.07 | 1.12 | 88 | 100 |
| | 0.28 | — | 0 | 0 |
| | 0.28 | 0.07 | 0 | 98 |
| | 0.28 | 0.28 | 0 | 100 |
| | 0.28 | 1.12 | 60 | 100 |
| | 1.12 | — | 0 | 0 |
| | 1.12 | 0.07 | 0 | 100 |
| | 1.12 | 0.28 | 0 | 100 |
| | 1.12 | 1.12 | 20 | 100 |
| 16 | 0.28 | — | 0 | 0 |
| | 0.28 | 0.07 | 0 | 100 |
| | 0.28 | 0.28 | 38 | 100 |
| | 0.28 | 1.12 | 93 | 100 |
| | 1.12 | — | 0 | 0 |
| | 1.12 | 0.07 | 0 | 100 |
| | 1.12 | 0.28 | 3 | 100 |
| | 1.12 | 1.12 | 58 | 100 |

[1]This test also included application of the herbicide at a rate of 0.018 kilograms per hectare, but the individual data was not included here since the herbicide alone caused no inhibition of rice plants at this rate in this test.

TABLE XIII[2]

| SAFENING AGENT | SAFENING AGENT RATE | HERBICIDE RATE | PERCENT INHIBITION RICE | PERCENT INHIBITION BARNYARDGRASS |
|---|---|---|---|---|
| | | 0.28 | 40 | 100 |
| | | 1.12 | 98 | 100 |
| 16 | 0.07 | — | 0 | 0 |
| | 0.07 | 0.28 | 30 | 100 |
| | 0.07 | 1.12 | 78 | 100 |
| | 0.28 | — | 0 | 0 |
| | 0.28 | 0.28 | 15 | 100 |
| | 0.28 | 1.12 | 53 | 100 |
| | 1.12 | — | 0 | 0 |
| | 1.12 | 0.28 | 0 | 100 |
| | 1.12 | 1.12 | 3 | 100 |

[2]This est also included application of the herbicide at rates of 0.018 and 0.07 kilograms per hectare, but the individual data was not included here since the herbicide alone caused no inhibition of rice plants at this rate in this test.

TABLE XIV[3]

| SAFENING AGENT | SAFENING AGENT RATE | HERBICIDE RATE | PERCENT INHIBITION RICE | PERCENT INHIBITION BARNYARDGRASS |
|---|---|---|---|---|
| | | 0.14 | 53 | 99 |
| | | 0.28 | 69 | 100 |
| | | 0.56 | 88 | 100 |
| | | 1.12 | 98 | 100 |
| 16 | 0.07 | — | 0 | 0 |
| | 0.07 | 0.14 | 10 | 100 |
| | 0.07 | 0.28 | 25 | 100 |
| | 0.07 | 0.56 | 83 | 100 |
| | 0.07 | 1.12 | 97 | 100 |
| | 0.28 | — | 0 | 0 |
| | 0.28 | 0.14 | 0 | 100 |
| | 0.28 | 0.28 | 0 | 100 |
| | 0.28 | 0.56 | 10 | 100 |
| | 0.28 | 1.12 | 55 | 100 |
| | 1.12 | — | 0 | 0 |
| | 1.12 | 0.14 | 0 | 100 |
| | 1.12 | 0.28 | 0 | 100 |
| | 1.12 | 0.56 | 0 | 100 |
| | 1.12 | 1.12 | 3 | 100 |

[3]This test also included application of the herbicide at a rate of 0.07 kilograms per hectare, but the individual data was not included here since the herbicide alone caused no inhibition of rate plants at this rate in this test.

EXAMPLE 9

A good grade of top soil was placed in a plastic pot and compacted to a depth of approximately 1.27 cm. from the top of said pot. A predetermined number of sorghum, crabgrass, barnyardgrass and foxtail seeds were placed on top of the soil. A cover layer, approximately 1.27 cm., was placed on top of said seeds. The soil was then treated with a tank mixture of a safening agent and a formulated 2-chloro-2',6'-diethyl-N-(methoxymethyl)acetanilide dispersed or dissolved in a suitable solvent. The pots were given overhead water and subirrigated as required for the duration of the test. The percent inhibition was observed approximately 21 days after treatment.

Tables XV–XVII summarize the results of three separate tests conducted in accordance with this procedure.

TABLE XV[3]

| SAFENING AGENT | SAFENING AGENT RATE | HERBICIDE RATE | Percent Inhibition ||||
|---|---|---|---|---|---|---|
| | | | SORGHUM | CRABGRASS | FOXTAIL | BARNYARD GRASS |
| | | 0.14 | 33 | 99 | 100 | 100 |
| | | 0.56 | 50 | 99 | 100 | 100 |
| | | 2.24 | 95 | 100 | 100 | 100 |
| 12 | 0.14 | — | 0 | 0 | 0 | 0 |
| | 0.14 | 0.14 | 10 | 99 | 99 | 99 |
| | 0.14 | 0.56 | 80 | 99 | 100 | 100 |
| | 0.14 | 2.24 | 95 | 100 | 100 | 100 |
| | 0.56 | — | 0 | 0 | 0 | 10 |
| | 0.56 | 0.14 | 10 | 99 | 100 | 99 |
| | 0.56 | 0.56 | 73 | 99 | 100 | 99 |
| | 0.56 | 2.24 | 95 | 100 | 100 | 100 |
| | 2.24 | — | 0 | 0 | 0 | 0 |
| | 2.24 | 0.14 | 0 | 99 | 100 | 99 |
| | 2.24 | 0.56 | 40 | 100 | 100 | 99 |
| | 2.24 | 2.24 | 90 | 100 | 100 | 100 |

[3] This test also included application of the herbicide at a rate of 0.035 kilograms per hectare, but the individual data was not included here since the herbicide alone caused no inhibition of sorghum plants at this rate.

TABLE XVI[4]

| SAFENING AGENT | SAFENING AGENT RATE | HERBICIDE RATE | Percent Inhibition ||||
|---|---|---|---|---|---|---|
| | | | SORGHUM | CRABGRASS | FOXTAIL | BARNYARD GRASS |
| | | 0.56 | 35 | 99 | 99 | 100 |
| | | 2.24 | 87 | 99 | 100 | 100 |
| 14 | 0.14 | — | 10 | 0 | 0 | 0 |
| | 0.14 | 0.56 | 35 | 98 | 95 | 100 |
| | 0.14 | 2.24 | 75 | 99 | 100 | 100 |
| | 0.56 | — | 5 | 3 | 0 | 0 |
| | 0.56 | 0.56 | 47 | 98 | 97 | 100 |
| | 0.56 | 2.24 | 90 | 99 | 99 | 100 |
| | 2.24 | — | 10 | 3 | 0 | 0 |
| | 2.24 | 0.56 | 23 | 98 | 90 | 100 |
| | 2.24 | 2.24 | 67 | 99 | 99 | 100 |

[4] This test also included application of the herbicide at a rate of 0.035 and 0.14 kilograms per hectare, but the individual data was not included here since the herbicide alone caused no effective inhibition of sorghum plants at these rates.

TABLE XVII[5]

| SAFENING AGENT | SAFENING AGENT RATE | HERBICIDE RATE | Percent Inhibition ||||
|---|---|---|---|---|---|---|
| | | | SORGHUM | CRABGRASS | FOXTAIL | BARNYARD GRASS |
| | | 0.14 | 68 | 40 | 98 | 99 |
| | | 0.56 | 93 | 83 | 99 | 100 |
| | | 2.24 | 98 | 99 | 100 | 100 |
| 16 | 0.14 | — | 0 | 0 | 35 | 0 |
| | 0.14 | 0.14 | 80 | 43 | 90 | 98 |
| | 0.14 | 0.56 | 83 | 84 | 99 | 100 |
| | 0.14 | 2.24 | 98 | 97 | 99 | 100 |
| | 0.56 | — | 0 | 0 | 5 | 48 |
| | 0.56 | 0.14 | 18 | 35 | 94 | 100 |
| | 0.56 | 0.56 | 93 | 73 | 100 | 100 |
| | 0.56 | 2.24 | 92 | 98 | 100 | 100 |
| | 2.24 | — | 0 | 0 | 0 | 45 |
| | 2.24 | 0.14 | 0 | 48 | 93 | 100 |
| | 2.24 | 0.56 | 48 | 78 | 99 | 100 |
| | 2.24 | 2.24 | 95 | 97 | 100 | 100 |

[5] This test also included application of the herbicide at a rate of 0.035 kilograms per hectare, but the individual data was not included here since the herbicide alone caused no inhibition of sorghum plants at this rate.

As noted above, crop plants may be protected from herbicidal injury by treating the crop seed with the safening agent prior to planting. Examples 10 and 11 illustrate such activity.

EXAMPLE 10

Dichloromethane solutions containing various concentrations of a safening agent of this invention were prepared and used to treat rice seeds. The treated seeds were then pregerminated for 2 days on moist towels. A plastic pot was partially filled with a good grade of top soil. Barnyardgrass was seeded into the soil, after which the pot was filled with additional soil, and formulated 2-chloro-2',6'-diethyl-N-(butoxymethyl)acetanilide herbicide dispersed or dissolved in a suitable carrier was sprayed on the soil surface. The pot was flooded and seeded with the pregerminated rice. The water level was lowered to the soil surface after 24 hours, and it was held at or below this level for 5–7 days. The pot was then reflooded for the duration of the test, and observations were made at the end of approximately 21 days.

The results in Table XVIII show that seed treatment with a safening agent will serve to reduce the inhibition of rice plants upon application of 2-chloro-2',6'-diethyl- N-(butoxymethyl)acetanilide while maintaining a high level of weed control. The application rate for the safening agent is given in terms of % weight of safening agent relative to seed weight.

TABLE XVIII

| SAFENING AGENT | SAFENING AGENT RATE | HERBICIDE RATE | PERCENT INHIBITION | |
|---|---|---|---|---|
| | | | RICE | BARNYARDGRASS |
| | | 0.018 | 13 | 89 |
| | | 0.07 | 28 | 97 |
| | | 0.28 | 96 | 100 |
| | | 1.12 | 100 | 100 |
| 16 | 0.035 | — | 0 | 0 |
| | 0.035 | 0.018 | 0 | 95 |
| | 0.035 | 0.07 | 0 | 99 |
| | 0.035 | 0.28 | 8 | 100 |
| | 0.035 | 1.12 | 58 | 100 |
| | 0.14 | — | 38 | 0 |
| | 0.14 | 0.018 | 40 | 83 |
| | 0.14 | 0.07 | 45 | 95 |
| | 0.14 | 0.28 | 45 | 100 |
| | 0.14 | 1.12 | 65 | 100 |
| | 0.56 | — | 98 | 13 |
| | 0.56 | 0.018 | 88 | 93 |
| | 0.56 | 0.07 | 88 | 97 |
| | 0.56 | 0.28 | 90 | 100 |
| | 0.56 | 1.12 | 93 | 100 |

EXAMPLE 11

Sorghum seeds were treated with a solution of the appropriate safening agent in dichloromethane. The solvent was evaporated which left only the safening agent on the seed. Untreated and treated sorghum seeds were planted in pots. Selected weed species were planted in separate pots. A 1.27 cm. deep soil cover layer was placed on the pre-seeded pots. The soil surface was then treated with formulated 2-chloro-2',6'-diethyl-N-(methoxymethyl)acetanilide. The pots were given overhead water and subirrigated as required for the duration of the test. Approximately 21 days later, the results were observed and recorded.

The results in Tables XIX and XX show that seed treatment with a safening agent will serve to reduce the inhibition of sorghum plants upon application of 2-chloro-2',6'-diethyl-N-(methoxymethyl)acetanilide while maintaining a high level of weed control. The application rate for the safening agent is given in terms of percent weight of safening agent relative to seed weight.

TABLE XIX

| SAFENING AGENT | SAFENING AGENT RATE | HERBICIDE RATE | PERCENT INHIBITION SORGHUM |
|---|---|---|---|
| | | 0.14 | 5 |
| | | 0.56 | 33 |
| | | 2.24 | 58 |
| 14 | 0.07 | — | 0 |
| | 0.07 | 0.14 | 3 |
| | 0.07 | 0.56 | 8 |
| | 0.07 | 2.24 | 50 |
| | 0.28 | — | 5 |
| | 0.28 | 0.14 | 20 |
| | 0.28 | 0.56 | 38 |
| | 0.28 | 2.24 | 38 |
| | 1.12 | — | 100 |
| | 1.12 | 0.14 | 100 |
| | 1.12 | 0.56 | 100 |
| | 1.12 | 2.24 | 100 |

| HERBICIDE RATE | PERCENT INHIBITION | | | | | | |
|---|---|---|---|---|---|---|---|
| | REDROOT PIGWEED | GREEN FOXTAIL | CRABGRASS | BARNYARD GRASS | PANICUM | WILD CANE | SORGHUM |
| 0.14 | 98 | 99 | 99 | 99 | 99 | 93 | 23 |
| 0.56 | 97 | 99 | 99 | 99 | 99 | 93 | 65 |
| 2.24 | 100 | 100 | 100 | 100 | 100 | 99 | 80 |

TABLE XX

| SAFENING AGENT | SAFENING AGENT RATE | HERBICIDE RATE | PERCENT INHIBITION SORGHUM |
|---|---|---|---|
| | | 0.28 | 90 |
| | | 1.12 | 97 |
| | | 4.48 | 99 |
| 21 | 0.07 | — | 0 |
| | 0.07 | 0.28 | 50 |
| | 0.07 | 1.12 | 73 |
| | 0.07 | 4.48 | 90 |
| | 0.28 | — | 5 |
| | 0.28 | 0.28 | 18 |
| | 0.28 | 1.12 | 20 |
| | 0.28 | 4.48 | 50 |
| | 1.12 | — | 80 |
| | 1.12 | 0.28 | 75 |
| | 1.12 | 1.12 | 73 |
| | 1.12 | 4.48 | 88 |

TABLE XX-continued

| HERBICIDE RATE | PERCENT INHIBITION | | | | | |
|---|---|---|---|---|---|---|
| | SMARTWEED | FOXTAIL | CRABGRASS | PANICUM | BARNYARD GRASS | SORGHUM |
| 0.07 | 30 | 90 | 95 | 95 | 98 | 60 |
| 0.28 | 80 | 98 | 99 | 99 | 99 | 83 |
| 1.12 | 90 | 99 | 99 | 99 | 100 | 96 |
| 4.48 | 98 | 100 | 100 | 100 | 100 | 98 |

Most of the preceding examples show the use of the described test procedures with more than one safening agent of this invention. It should be understood that all of the tests within a single example were not necessarily conducted at the same time. It should also be understood, than an untreated container, plus containers with the herbicide alone and the safening agent alone, are employed for each test initiation date. These are the controls used to obtain the herbicide and safening effect data for tests begun on that particular date.

The above examples illustrate that while the 5-(aryl)-4-isoxazolecarboxylates of the invention generally safen crop plants, especially rice, sorghum and wheat crops to the herbicidal effects of acetanilide herbicides, those skilled in the art will appreciate that the compounds of the invention may be used most effectively in safening sorghum against injury due to 2-chloro-2',6'-diethyl-N-(methoxymethyl)acetanilide and 2-chloro-N-(2-methoxy-1-methylethyl)-6'-ethyl-o-acetotoluidide, and rice against the herbicidal effects of 2-chloro-2',6'-diethyl-N-(butoxymethyl)acetanilide.

The herbicide, safening agent or mixture thereof may be applied to the plant locus alone or the herbicide, safening agent or mixture thereof may be applied in conjunction with a material referred to in the art as an adjuvant in liquid or solid form. Mixtures containing the appropriate herbicide and safening agent usually are prepared by admixing said herbicide and safening agent with an adjuvant including diluents, extenders, carriers and conditioning agents to provide compositions in the form of finely-divided particulate solids, granules, pellets, wettable powders, dusts, solutions and aqueous dispersions or emulsions. Thus, the mixture may include an adjuvant such as a finely-divided particulate solid, a solvent liquid of organic origin, water, a wetting agent, dispersing agent, or emulsifying agent or any suitable combination of these.

When applying the herbicide, safening agent or mixture thereof to the plant locus useful finely-divided solid carriers and extenders include, for example, the talcs, clays, pumice, silica, diatomaceous earth, quartz, Fullers earth, sulfur, powdered cork, powdered wood, walnut flour, chalk, tobacco dust, charcoal and the like. Typical liquid diluents useful include for example, Stoddard solvent, acetone, alcohols, glycols, ethyl acetate, benzene and the like. Such compositions, particularly liquids and wettable powders, usually contain as a conditioning agent one or more surface-active agents in amounts sufficient to render a given composition readily dispersible in water or in oil. By the term "surface-active agent", it is understood that wetting agents, dispersing agents, suspending agents and emulsifying agents are included therein. Such surface-active agents are well known and reference is made to U.S. Pat. No. 2,547,724, Columns 3 and 4, for detailed examples of the same.

Compositions of this invention generally contain from about 5 to 95 parts herbicide and safening agent, about 1 to 50 parts surface-active agent and about 4 to 94 parts solvent, all parts being by weight based on the total weight of the composition.

The application of the herbicide, safening agent or mixture thereof in a liquid or particulate solid form can be carried out by conventional techniques utilizing, for example, spreaders, power dusters, boom and hand sprayers, spray dusters and granular applications. The compositions can also be applied from airplanes as a dust or spray. If desired, application of the compositions of the invention to plants can be accomplished by incorporating the compositions in the soil or other media.

The above examples also illustrate that the crop may be protected by treating the crop seed with an effective amount of safening agent prior to planting. Generally, small amounts of safening agent are required to treat such seeds. Examples 10 and 11 illustrate that a weight ratio of as little as 0.6 parts of safener per 1000 parts of seed may be effective. The amount of safener utilized in treating the seed may be increased if desired. Generally, however, a weight ratio of safening agent to seed weight may range from 0.1 to 10.0 parts of safening agent per 1000 parts of seed. The determination of the effective amount of safening agent required is well within the skill of the art.

Since only a very small amount of active safening agent is usually required for the seed treatment, the safening agent preferably is formulated as a powder or an emulsifiable concentrate which can be diluted with water by the seed treater for use in the seed treating apparatus. Of course, under certain conditions, it may be desirable to dissolve the safening agent in an organic solvent for use as a seed treatment or the pure compound alone may be used under properly controlled conditions.

There are thus also provided by this invention novel seed treating compositions containing one or more of the described active safening agents intimately dispersed in an inert carrier or diluent for the intended use. Such carriers may be either solids, such as talc, clay, diatomaceous earth, sawdust, calcium carbonate, and the like or liquids such as water, kerosene, acetone, benzene, toluene, xylene, and the like in which the active agent may be either dissolved or dispersed. Emulsifying agents are advisably used to achieve a suitable emulsion if two immiscible liquids are used as a carrier. Wetting agents may also be used to aid in dispersing the active safening agent in liquids used as a carrier in which the agent is not completely soluble. Emulsifying agents and wetting agents are sold under numerous tradenames and may be either pure compounds, mixtures of compounds of the same general groups, or they may be mixtures of compounds of different classes. Typical satisfactory surface-active agents which may be used are alkali metal, higher alkylarylsulfonates such as sodium dodecylbenzenesulfonate and the sodium salts of alkylnaphthalenesulfonic acids, fatty alcohol sulfates such as the sodium salts of monoesters of sulfuric acid with n-aliphatic alcohols containing 8–18 carbon atoms, long chain quaternary ammonium compounds, sodium salts of petroleum-derived alkylsulfonic acids, polyethylene sorbitan monooleate, alkylaryl polyether alcohols, water-soluble lignin sulfonate salts, alkali-casein compositions, long chain alcohols usually containing 10–18 carbon atoms, and condensation products of ethylene oxide with fatty acids, alkylphenols and mercaptans.

Certain 5-aryl-4-isoxazolecarboxylic acids and their derivatives are known in the art. The preparation of 5-phenylisoxazole-4-carboxylic acid is disclosed in Chemical Abstracts 53, 9187i. The preparation of ethyl-5-phenyl-4-isoxazole carboxylate is described in Chem. Ber. 106, 3291 (1973). However, neither reference suggests any possible utility for the above-mentioned compounds.

In accordance with this invention, the 5-aryl-4-isoxazolecarboxylates and derivatives thereof are produced by the following general procedure:

An ethyl-2-(substituted benzoyl)-3-dimethylaminopropenoate is reacted with hydroxylamine hydrochloride in the presence of sodium acetate to produce the ethyl-5-aryl-4-isoxazolecarboxylate. The process can be conducted within a temperature range of 0°–100° C. with reflux conditions being preferred. Although not narrowly critical, a reaction time of 1 to 3 hours is sufficient to complete the reaction. Solvents such as methanol, ethanol, dioxane, tetrahydrofuran and a mixture of methanol, and diethyl ether are preferred.

To prepare the 5-aryl-4-isoxazolecarboxylic acid, the ethyl-5-aryl-4-isoxazolecarboxylate is treated with concentrated hydrochloric acid. Reflux conditions and a reaction time of 1 to 6 hours is generally preferred to complete the reaction. Solvents such as glacial acetic acid, dioxane and tetrahydrofuran are preferred.

Treatment of the 5-aryl-4-isoxazolecarboxylic acid with thionylchloride yields the 5-aryl-4-isoxazolecarbonylchloride which subsequently reacts with an appropriate alcohol to produce the ester derivative of 5-aryl-4-isoxazolecarboxylic acid. The process is conducted under anhydrous conditions and within a temperature range of 0°–100° C. Although not narrowly critical, a reaction time of 2 to 9 hours is generally preferred to complete the reaction. Solvents such as benzene, toluene and the like are preferred.

In order to fully illustrate the manner in which the 5-aryl-4-isoxazolecarboxylates of the present invention are prepared, the following examples are presented.

EXAMPLE 12

Hydroxylamine hydrochloride (1.1 g.; 0.016 mol.) was added to a mixture of ethyl-2-(2',4'-dichlorobenzoyl)-3-dimethylaminopropenoate (4.74 g.; 0.015 mol.) and anhydrous sodium acetate (1.25 g.; 0.015 mol.) in 50 ml. of ether and 25 ml. of methanol at 25° C. An additional 25 ml. of methanol was added, and the resultant mixture was stirred for 30 minutes. The mixture was washed into a separatory funnel with 150 ml. of ether and the ether layer was washed free of salts with water. The ether layer was dried with magnesium sulfate, filtered, then concentrated to yield an oil which was crystallized from pentane to yield ethyl-5-(2',4'-dichlorophenyl)-4-isoxazolecarboxylate (1.88 g.; 44% yield) as tan crystals having a melting point of 82°–84° C. and the following analysis:

CALCULATED: C, 50.83; H, 3.17; N, 4.90; Cl, 24.78. FOUND: C, 50.25; H, 3.19; N, 4.96; Cl, 24.80.

EXAMPLE 13

The procedure of Example 12 was employed utilizing ethyl-2-(3'-anisoyl)-3-dimethylaminopropenoate in lieu of ethyl-2-(2',4'-dichlorobenzoyl)-3-dimethylaminopropenoate to yield ethyl-5-(3'-methoxyphenyl)-4-isoxazolecarboxylate (2.3 g.; 62% yield) as yellow crystals having a melting point of 85°–87° C. and the following analysis:

CALCULATED: C, 63.15; H, 5.30; N, 5.67. FOUND: C, 63.26; H, 5.25; N, 5.72.

EXAMPLE 14

The procedure of Example 12 was employed utilizing ethyl-2-(4'-trifluoromethylbenzoyl)-3-dimethylaminopropenoate in lieu of ethyl-2-(2',4'-dichlorobenzoyl)-3-dimethylaminopropenoate to yield ethyl-5-(4'-trifluoromethylphenyl)-4-isoxazolecarboxylate (2.03 g.; 47% yield) as yellow crystals having a melting point of 42°–44° C. and the following analysis:

CALCULATED: C, 54.74; H, 3.53; N, 4.91; F, 19.98. FOUND: C, 54.65; H, 3.43; N, 4.80; F, 20.05.

EXAMPLE 15

Hydroxylamine hydrochloride (1.1 g.; 0.016 mol.) was added to a mixture of ethyl-2-benzoyl-3-dimethylaminopropenoate (3.71 g.; 0.015 mol.) and anhydrous sodium acetate (1.25 g.; 0.015 mol.) in 50 ml. of ether and 25 ml. of methanol at 25° C. After 16 hours, the solvent was removed by evaporation and the residue was extracted with five 50 ml. portions of ether. The ether extracts were combined, washed with water, dried, filtered, then concentrated to yield an oil which was further purified by evaporative distillation at 60° C. and 0.55 torr. to yield ethyl-5-phenyl-4-isoxazolecarboxylate (1.03 g.; 32% yield) as a colorless liquid having the following analysis:

CALCULATED: C, 66.25; H, 5.10; N, 6.45. FOUND: C, 66.33; H, 5.13; N, 6.67.

EXAMPLE 16

The procedure of Example 15 was employed utilizing ethyl-2-(4'-chlorobenzoyl)-3-dimethylaminopropenoate in lieu of ethyl-2-benzoyl-3-dimethylaminopropenoate to yield ethyl-5-(4'-chlorophenyl)-4-isoxazolecarboxylate (3.7 g.; 49% yield) having a melting point of 58°–60° C. and the following analysis:

CALCULATED: C, 57.27; H, 4.01; N, 5.57; Cl, 14.09. FOUND: C, 57.38; H, 4.05; N, 5.37; Cl, 13.97.

EXAMPLE 17

The procedure of Example 15 was employed utilizing ethyl-2-(4-toluyl)-3-dimethylaminopropenoate in lieu of ethyl-2-benzoyl-3-dimethylaminopropenoate to yield ethyl-5-(4'-methylphenyl)-4-isoxazolecarboxylate (2.03 g.; 59% yield) having a melting point of 42°–44° C. and the following analysis:

CALCULATED: C, 67.52; H, 5.67; N, 6.06. FOUND: C, 67.69; H, 5.66; N, 6.04.

EXAMPLE 18

The procedure of Example 15 was employed utilizing ethyl-2-(3'-chlorobenzoyl)-3-dimethylaminopropenoate in lieu of ethyl-2-benzoyl-3-dimethylaminopropenoate to yield ethyl-5-(3'-chlorophenyl)-4-isoxazolecarboxylate (3.2 g.; 51% yield) having a melting point of 75°–77° C. and the following analysis:

CALCULATED: C, 57.27; H, 4.01; N, 5.57; Cl, 14.09. FOUND: C, 57.40; H, 4.02; N, 5.43; Cl, 13.98.

EXAMPLE 19

The procedure of Example 15 was employed utilizing ethyl-2-(4'-methoxybenzoyl)-3-dimethylaminopropenoate in lieu of ethyl-2-benzoyl-3-dimethylaminopropenoate to yield ethyl-5-(4'-methoxyphenyl)-4-isoxazolecarboxylate (1.5 g.; 61% yield) having a melting point of 57°–59° C. and the following analysis:
CALCULATED: C, 63.15; H, 5.30; N, 5.67. FOUND: C, 63.56; H, 5.35; N, 5.79.

EXAMPLE 20

Hydroxylamine hydrochloride (0.7 g.; 0.01 mol.) was added to a mixture of ethyl-2-(3',4'-dichlorobenzoyl)-3-di-methylaminopropenoate (3.16 g.; 0.01 mol.) and sodium acetate (0.82 g.; 0.01 mol.) in 25 ml. of diethyl ether and 15 ml. of methanol. The resultant mixture was stirred at 25° C. for 16 hours until the reaction was complete. The reaction mixture was filtered and concentrated in vacuo. The residue was dissolved in chloroform, extracted with water, dried over magnesium sulfate and concentrated in vacuo. Recrystallization with ethanol yielded ethyl-5-(3',4'-dichlorophenyl)-4-isoxazolecarboxylate as a white solid (1.5 g.; 52.4% yield) having a melting point of 108°–110° C. and the following analysis:
CALCULATED: C, 50.37; H, 3.17; N, 4.89. FOUND: C, 50.32; H, 3.21; N, 4.88.

EXAMPLE 21

The procedure of Example 20 was employed utilizing ethyl-2-(4'-fluorobenzoyl)-3-dimethylaminopropenoate in lieu of ethyl-2-(3',4'-dichlorobenzoyl)-3-dimethylaminopropenoate to yield upon recrystallization with pentane, ethyl-5-(4'-fluorophenyl)-4-isoxazolecarboxylate (1.75 g.; 74.5% yield) as a white solid having a melting point of 34°–38° C. and the following analysis:
CALCULATED: C, 61.27; H, 4.29; N, 5.96. FOUND: C, 61.25; H, 4.29; N, 5.98.

EXAMPLE 22

Ethyl-2-(2'-chlorobenzoyl)-3-dimethylaminopropenoate (2.81 g.; 0.01 mol.) was dissolved in 15 ml. of dioxane. To this solution was added a solution of hydroxylamine hydrochloride (1.05 g.; 0.015 mol.) in 5 ml. of water. The resulting solution was stirred for 14 hours at 25° C. Water was added to precipitate ethyl-5-(2'-chlorophenyl)-4-isoxazolecarboxylate as an oil (0.7 g.; 19.9% yield) having the following analysis:
CALCULATED: C, 57.27; H, 4.01. FOUND: C, 57.17; H, 4.04.

EXAMPLE 23

The procedure of Example 22 was employed utilizing ethyl-2-(2'-methylbenzoyl)-3-dimethylaminopropenoate in lieu of ethyl-2-(2'-chlorobenzoyl)-3-dimethylaminopropenoate to yield ethyl-5-(2'-methylphenyl)-4-isoxazolecarboxylate (1.9 g.; 82.6% yield) as an oil having the following analysis:
CALCULATED: C, 67.52; H, 5.67. FOUND: C, 67.37; H, 5.69.

EXAMPLE 24

Ethyl-2-(2'-trifluoromethylbenzoyl)-3-dimethylaminopropenoate (3.14 g.; 0.01 mol.) was dissolved in 15 ml. of dioxane. To this solution was added a solution of hydroxylamine hydrochloride (1.05 g.; 0.015 mol.) in 5 ml. of water. The resulting solution was stirred for 14 hours at 25° C. Extraction with water and diethyl ether yielded ethyl-5-(2'-trifluoromethylphenyl)-4-isoxazolecarboxylate as an oil (1.6 g.; 56.2% yield) having the following analysis:
CALCULATED: C, 54.74; H, 3.53. FOUND: C, 54.89; H, 3.75.

EXAMPLE 25

Hydroxylamine hydrochloride (0.69 g.; 0.01 mol.) was added to a mixture of ethyl-2-(4'-nitrobenzoyl)-3-dimethylaminopropenoate (2.93 g.; 0.01 mol.) and anhydrous sodium acetate (0.82 g.; 0.01 mol.) in 50 ml. of tetrahydrofuran and 25 ml. of methanol. The resultant mixture was stirred at 25° C. for 16 hours until the reaction was complete. The reaction mixture was filtered and the solvent removed from the filtrate by concentration in vacuo. The residue was dissolved in chloroform, extracted with water, dried over magnesium sulfate and then concentrated in vacuo. Recrystallization with ethanol yielded ethyl-5-(4'-nitrophenyl)-4-isoxazolecarboxylate as a white solid (1.2 g.; 45.8% yield) having a melting point of 73°–76° C. and the following analysis:
CALCULATED: C, 54.96; H, 3.84; N, 10.69. FOUND: C, 54.93; H, 3.84; N, 10.70.

EXAMPLE 26

A mixture of methyl-2-(3'-trifluoromethylbenzoyl)-3-ethoxypropenoate (8.55 g.; 0.028 mol.) in 60 ml. of ethanol and anhydrous sodium acetate (2.5 g.; 0.03 mol.) was treated with hydroxylamine hydrochloride (2.1 g.; 0.03 mol.). The mixture was heated at reflux for 2 hours, cooled to 25° C., and then poured onto 50 g. of ice. The resulting liquid was extracted five times with 40 ml. of methylene chloride. The organic layer was washed with water, sodium bicarbonate, water, dried over sodium sulfate, filtered and concentrated to yield methyl-5-(3'-trifluoromethylphenyl)-4-isoxazolecarboxylate as an orange oil.

A portion of the methyl-5-(3'-trifluoromethylphenyl)-4-isoxazolecarboxylate (5.0 g.; 0.018 mol.) in 10 ml. of acetic acid was reacted with 10 ml. of concentrated hydrochloric acid at reflux for six hours. The reaction mixture was cooled to 25° C., and then poured onto 50 g. of ice. The resulting mixture was extracted five times with 25 ml. of methylene chloride. The extracts were combined, dried over magnesium sulfate, filtered, and concentrated to yield a white solid. Recrystallization from ether-hexane yielded 5-(3'-trifluoromethylphenyl)-4-isoxazolecarboxylic acid.

A portion of the 5-(3'-trifluoromethylphenyl)-4-isoxazolecarboxylic acid (2.5 g.; 0.01 mol.) in 25 ml. of ethanol and 2 ml. of sulfuric acid were heated at reflux for 4 hours. The reaction mixture was cooled, concentrated to one-half its initial volume, then diluted with 175 ml. of methylene chloride. The organic solution was washed with water, sodium bicarbonate, again with water, dried over magnesium sulfate, filtered and concentrated to give an oil. The oil was distilled through a Vigreux column to yield ethyl-5-(3'-trifluoromethylphenyl)-4-isoxazolecarboxylate (2.2 g.; 80% yield) as a colorless oil (b.p.=88°–90° C. at 0.15 torr.) having the following analysis:
CALCULATED: C, 54.74; H, 3.53; N, 4.91; F, 19.98. FOUND: C, 54.69; H, 3.42; N, 5.08; F, 20.16.

EXAMPLE 27

Ethyl-5-(2',4'-dichlorophenyl)-4-isoxazolecarboxylate (50.0 g.; 0.17 mol.) was dissolved in 250 ml. of glacial acetic acid. To the mixture was added 250 ml. of hydrochloric acid and the resultant solution was rapidly stirred at 100° C. for 4 hours. The mixture was then allowed to cool and poured into 2 liters of water. The resultant precipitate was collected, dried, and recrystallized from pentane to yield 5-(2',4'-dichlorophenyl)-4-isoxazolecarboxylic acid (40.0 g.; 93.6% yield) having a melting point of 122°–123° C. and the following analysis:

CALCULATED: C, 46.70; H, 1.96; N, 5.45; Cl, 27.57. FOUND: C, 46.63; H, 1.99; N, 5.41; Cl, 27.44.

EXAMPLE 28

The procedure of Example 27 was employed utilizing ethyl-5-phenyl-4-isoxazolecarboxylate in lieu of ethyl-5-(2',4'-dichlorophenyl)-4-isoxazolecarboxylate to yield upon recrystallization with toluene, 5-phenyl-4-isoxazolecarboxylic acid (7.5 g.; 55% yield) as a white solid having a melting point of 153°–154° C. and the following analysis:

CALCULATED: C, 63.49; H, 3.73; N, 7.40. FOUND: C, 63.44; H, 3.78; N, 7.39.

EXAMPLE 29

5-(2',4'-Dichlorophenyl)-4-isoxazolecarboxylic acid 20.0 g.; 0.078 mol.) was covered with 20 ml. of thionyl chloride and the mixture heated on a steam cone for 3 hours. The excess thionyl chloride was then removed in vacuo and the oily residue was recrystallized from pentane to yield the 5-(2',4'-dichlorophenyl)-4-isoxazolecarbonyl chloride (15.2 g.; 70.7% yield) having a melting point of 46°–50° C. and the following analysis:

CALCULATED: C, 43.43; H, 1.46; Cl, 38.47. FOUND: C, 43.50; H, 1.50; Cl, 38.47.

EXAMPLE 30

5-(2',4'-Dichlorophenyl)-4-isoxazolecarbonyl chloride (2.0 g.; 0.007 mol.) was covered with 2-(2'-methoxyethoxy) ethanol and the solution was heated on a steam cone for 2 hours. After esterification, the excess 2-(2'-methoxyethoxy) ethanol was extracted into water. The insoluble oil was dissolved in ether, dried with anhydrous magnesium sulfate and concentrated to yield 2-(2'-methoxyethoxy)ethyl-5-(2',4'-dichlorophenyl)-4-isoxazolecarboxylate (2.4 g.; 96% yield) as an oil having the following analysis:

CALCULATED: C, 50.01; H, 4.19. FOUND: C, 49.96; H, 4.25.

EXAMPLE 31

5-(2',4'-Dichlorophenyl)-4-isoxazolecarbonyl chloride (17.6 g.; 0.078 mol.) dissolved in 50 ml. of tetrahydrofuran was added dropwise over a period of one hour to a cold solution of ammonia in tetrahydrofuran which had been prepared by bubbling ammonia through 70 ml. of tetrahydrofuran cooled in a dry ice-acetone bath. The mixture was allowed to warm to 25° C. then stirred for 30 minutes. The resultant mixture was filtered and the filtrate was stripped of solvent to yield a white solid which was recrystallized from toluene to yield 5-(2',4'-dichlorophenyl)-4-isoxazole (14.8 g.; 74% yield) having a melting point of 116°–118° C. and the following analysis:

CALCULATED: C, 46.72; H, 2.35; N, 10.90. FOUND: C, 46.60; H, 2.39; N, 10.85.

EXAMPLE 32

5-(2',4'-Dichlorophenyl)-4-isoxazolecarbonyl chloride (2.0 g.; 0.007 mol.) was covered with methanol and the solution was heated on a steam cone for 2 hours. The excess methanol was then removed under reduced pressure and the resulting residue was dissolved in hot pentane. The product crystallized from the pentane solution to yield methyl-5-(2',4'-dichlorophenyl)-4-isoxazolecarboxylate (1.2 g.; 63.1% yield) having a melting point of 83°–84° C. and the following analysis:

CALCULATED: C, 48.55; H, 2.59; N, 5.15. FOUND: C, 48.41; H, 2.61; N, 5.13.

Utilizing the appropriate alcohol and the procedure of Example 32, the following compounds have been prepared:

| EXAMPLE | COMPOUND | YIELD | M.P. | CALCULATED C | CALCULATED H | FOUND C | FOUND H |
|---|---|---|---|---|---|---|---|
| 33 | n-Propyl-5-(2',4'-dichlorophenyl)-4-isoxazolecarboxylate | 1.1 g; 52.4% | | 52.02 | 3.69 | 52.08 | 3.70 |
| 34 | 2-Methoxyethyl-5-(2',4'-dichlorophenyl)-4-isoxazolecarboxylate | 1.9 g; 86.4% | | 49.39 | 3.51 | 49.34 | 3.43 |
| 35 | Isopropyl-5-(2',4'-dichlorophenyl)-4-isoxazolecarboxylate | 1.4 g; 66.6% | 37–39° C. | 52.02 | 3.69 | 51.95 | 3.72 |
| 36 | n-Butyl-5-(2',4'-dichlorophenyl)-4-isoxazolecarboxylate | 1.3 g; 59.1% | | 53.52 | 4.17 | 53.33 | 4.00 |
| 37 | 2-Chloroethyl-5-(2',4'-dichlorophenyl)-4-isoxazolecarboxylate | 2.0 g; 89.3% | 65–67° C. | 44.96 | 2.50 | 44.95 | 2.50 |
| *38 | 2-Fluoroethyl-5-(2',4'-dichlorophenyl)-4-isoxazolecarboxylate | 1.2 g; 56.3% | 57–60° C. | 47.39 | 2.65 | 47.15 | 2.35 |

*Recrystallized from petroleum-ether.

Although this invention has been described with respect to specific modifications, the details thereof are not to be construed as limitations, for it will be apparent that various equivalents, changes and modifications may be resorted to without departing from the spirit and scope thereof and it is understood that such equivalent embodiments are intended to be included herein.

What is claimed is:

1. A composition comprising a herbicidally effective amount of an alpha-haloacetanilide herbicide and an effective safening amount of a compound having the formula

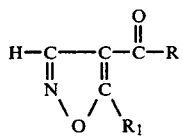

wherein R is selected from the group consisting of hydroxyl, lower alkoxy, lower alkoxyalkoxy, lower alkoxyalkoxyalkoxy, lower haloalkoxy, amino and halogen; and $R_1$ is selected from the group consisting of phenyl and phenyl substituted with up to three groups individually selected from the class consisting of lower alkyl, lower alkoxy, lower haloalkyl, nitro and halogen.

2. A composition according to claim 1 where the alpha-haloacetanilide herbicide is selected from the group consisting of 2-chloro-2',6'-diethyl-N-(methoxymethyl)acetanilide, 2-chloro-2',6'-diethyl-N-(butoxymethyl)acetanilide and 2-chloro-N-(2-methoxy-1-methylethyl)-6'-ethyl-o-acetotoluide.

3. A composition according to claim 2 wherein R is lower alkoxy.

4. A composition according to claim 3 wherein $R_1$ is phenyl substituted with up to three groups individually selected from the class consisting of lower alkyl, lower alkoxy, lower haloalkyl, nitro and halogen.

5. A composition according to claim 4 wherein R is ethoxy.

6. A composition according to claim 5 wherein said compound is ethyl-5-(4-chlorophenyl)-4-isoxazolecarboxylate.

7. A composition according to claim 6 wherein said herbicide is 2-chloro-2',6'-diethyl-N-(butoxymethyl)acetanilide.

8. A composition according to claim 5 wherein said compound is ethyl-5-(2,4-dichlorophenyl)-4-isoxazolecarboxylate.

9. A composition according to claim 8 wherein said herbicide is 2-chloro-2',6'-diethyl-N-(butoxymethyl)acetanilide.

10. A composition according to claim 5 wherein said compound is ethyl-5-(4-trifluoromethylphenyl)-4-isoxazolecarboxylate.

11. A composition according to claim 10 wherein said herbicide is 2-chloro-2',6'-diethyl-N-(methoxymethyl)acetanilide.

12. A method of reducing herbicidal injury to rice plants which comprises treating the plant locus with a herbicidally effective amount of 2-chloro-2',6'-diethyl-N-(butoxymethyl)acetanilide and an effective safening amount of a compound having the formula

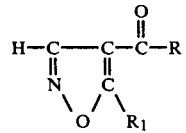

wherein R is selected from the group consisting of hydroxyl, lower alkoxy, lower alkoxyalkoxy, lower alkoxyalkoxyalkoxy, lower haloalkoxy and halogen; and $R_1$ is selected from the group consisting of phenyl and phenyl substituted with up to three groups individually selected from the class consisting of lower alkyl, lower alkoxy, lower haloalkyl, nitro and halogen; provided that when R is hydroxyl, $R_1$ is not phenyl, and further provided that when R is ethoxy, $R_1$ is not 4-methoxyphenyl or 2-methylphenyl.

13. A method according to claim 12 wherein R is lower alkoxy.

14. A method according to claim 13 wherein $R_1$ is phenyl substituted with up to three groups individually selected from the class consisting of lower alkyl, lower alkoxy, lower haloalkyl, nitro and halogen.

15. A method according to claim 14 wherein R is ethoxy.

16. A method according to claim 15 wherein said compound is ethyl-5-(4-chlorophenyl)-4-isoxazolecarboxylate.

17. A method according to claim 15 wherein said compound is ethyl-5-(2,4-dichlorophenyl)-4-isoxazolecarboxylate.

18. A method according to claim 12 wherein the weight ratio of said herbicide to said compound is from 1:32 to 32:1.

19. A method according to claim 12 wherein the weight ratio of said herbicide to said compound is from 1:8 to 8:1.

20. A method of reducing herbicidal injury to rice plants which comprises treating the plant locus with an effective amount of a mixture comprising a herbicidally effective amount of 2-chloro-2',6'-diethyl-N-(butoxymethyl)acetanilide and an effective safening amount of a compound of the formula

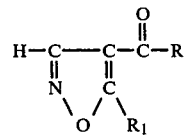

wherein R is selected from the group consisting of hydroxyl, lower alkoxy, lower alkoxyalkoxy, lower alkoxyalkoxyalkoxy, lower haloalkoxy and halogen; and $R_1$ is selected from the group consisting of phenyl and phenyl substituted with up to three groups individually selected from the class consisting of lower alkyl, lower alkoxy, lower haloalkyl, nitro and halogen; provided that when R is hydroxyl, $R_1$ is not phenyl, and further provided that when R is ethoxy, $R_1$ is not 4-methoxyphenyl or 4-methylphenyl.

21. A method according to claim 20 wherein R is lower alkoxy.

22. A method according to claim 21 wherein $R_1$ is phenyl substituted with up to three groups individually selected from the class consisting of lower alkyl, lower alkoxy, lower haloalkyl, nitro and halogen.

23. A method according to claim 22 wherein R is ethoxy.

24. A method according to claim 23 wherein said compound is ethyl-5-(4-chlorophenyl)-4-isoxazolecarboxylate.

25. A method according to claim 23 wherein said compound is ethyl-5-(2,4-dichlorophenyl)-4-isoxazolecarboxylate.

26. A method according to claim 20 wherein the weight ratio of said herbicide to said compound is from 1:32 to 32:1.

27. A method according to claim 20 wherein the weight ratio of said herbicide to said compound is from 1:8 to 8:1.

28. A method for reducing herbicidal injury to sorghum crop plants which comprises treating the plant locus with a herbicidally effective amount of 2-chloro-2',6'-diethyl-N-(methoxymethyl)acetanilide and an effective safening amount of a compound having the formula

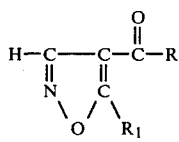

wherein R is selected from the group consisting of hydroxyl lower alkoxy containing two or more carbons, lower alkoxyalkoxy lower alkoxyalkoxyalkoxy, lower haloalkoxy and amino and $R_1$ is selected from the group consisting of phenyl and phenyl substituted with up to three groups individually selected from the class consisting of lower alkyl, lower haloalkyl and halogen; provided that when R is ethoxy, $R_1$ is not 4-methylphenyl or 3,4-dichlorophenyl and further provided that when R is hydroxyl, $R_1$ is not phenyl and further provided that when R is 2-fluoroethoxy, $R_1$ is not 2,4-dichlorophenyl.

29. A method according to claim 28 wherein R is lower alkoxy.

30. A method according to claim 29 wherein $R_1$ is phenyl substituted with up to three groups individually selected from the class consisting of lower alkyl, lower haloalkyl, and halogen.

31. A method according to claim 30 wherein R is ethoxy.

32. A method according to claim 31 wherein said compound is ethyl-5-(2,4-dichlorophenyl)-4-isoxazolecarboxylate.

33. A method according to claim 31 wherein said compound is ethyl-5-(4-trifluoromethylphenyl)-4-isoxazolecarboxylate.

34. A method according to claim 28 wherein the weight ratio of said herbicide to said compound is from 1:32 to 32:1.

35. A method according to claim 28 wherein the weight ratio of said herbicide to said compound is from 1:8 to 8:1.

36. A method of reducing herbicidal injury to sorghum crop plants which comprises treating the plant locus with an effective amount of a mixture comprising a herbicidally effective amount of a herbicide selected from the group consisting of 2-chloro-2',6'-diethyl-N-(methoxymethyl)acetanilide and 2-chloro-N-(2-methoxy-1-methylethyl)-6'-ethyl-o-acetotoluidide and an effective safening amount of a compound having the formula

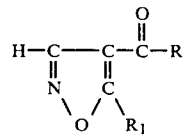

wherein R is selected from the group consisting of hydroxyl lower alkoxy containing two or more carbons, lower alkoxyalkoxy, lower alkoxyalkoxyalkoxy, lower haloalkoxy and amino and $R_1$ is selected from the group consisting of phenyl and phenyl substituted with up to three groups individually selected from the class consisting of lower alkyl, lower haloalkyl and halogen; provided that when R is ethoxy, $R_1$ is not 4-methylphenyl or 3,4-dichlorophenyl and further provided that when R is hydroxyl, $R_1$ is not phenyl and further provided that when R is 2-fluoroethoxy, $R_1$ is 2,4-dichlorophenyl.

37. A method according to claim 36 wherein R is lower alkoxy.

38. A method according to claim 37 wherein $R_1$ is phenyl substituted with up to three groups individually selected from the class consisting of lower alkyl, lower haloalkyl and halogen.

39. A method according to claim 38 wherein R is ethoxy.

40. A method according to claim 39 wherein said compound is ethyl-5-(2,4-dichlorophenyl)-4-isoxazolecarboxylate.

41. A method according to claim 39 wherein said compound is ethyl-5-(4-trifluoromethylphenyl)-4-isoxazolecarboxylate.

42. A method according to claim 36 wherein the weight ratio of said herbicide to said compound is from 1:32 to 32:1.

43. A method according to claim 36 wherein the weight ratio of said herbicide to said compound is from 1:8 to 8:1.

* * * * *